US005728363A

United States Patent [19]

Martin et al.

[11] Patent Number: 5,728,363
[45] Date of Patent: *Mar. 17, 1998

[54] TWO POWDER SYNTHESIS OF HYDROTALCITE AND HYDROTALCITE-LIKE COMPOUNDS

[75] Inventors: Edward S. Martin, New Kensington; John M. Stinson, Murrysville; William E. Horn, Jr., Gibsonia; Vito Cedro, III, Export, all of Pa.

[73] Assignee: Aluminum Company of America, Pittsburgh, Pa.

[*] Notice: The term of this patent shall not extend beyond the expiration date of Pat. No. 5,578,286.

[21] Appl. No.: 625,584

[22] Filed: Mar. 28, 1996

Related U.S. Application Data

[63] Continuation-in-part of Ser. No. 290,220, Aug. 15, 1994, abandoned, which is a continuation-in-part of Ser. No. 235,504, Apr. 29, 1994, Pat. No. 5,514,361.

[51] Int. Cl.$^6$ .............................. C07F 11/00; C07F 13/00
[52] U.S. Cl. .......................... 423/593; 423/306; 423/367; 423/395; 423/420.2; 423/463; 423/556; 423/557; 423/558; 423/594; 423/595; 423/599; 423/600; 534/15; 534/16; 556/1; 556/13; 556/15; 556/16; 556/19; 556/43; 556/44; 556/46; 556/49; 556/58; 556/61; 556/62; 556/87; 556/90; 556/112; 556/114; 556/121; 556/131; 556/140; 556/147

[58] Field of Search .................. 423/420.2, 593, 423/306, 367, 395, 463, 556, 557, 558, 594, 595, 599, 600; 534/15, 16, 1, 13, 19, 43, 44, 46; 556/49, 58, 61, 62, 87, 90, 112, 114, 121, 131, 140, 147

[56] References Cited

U.S. PATENT DOCUMENTS 5,399,329    3/1995    Schutz et al. .................. 423/415.1
5,578,286   11/1996    Martin et al. ..................... 423/594

*Primary Examiner*—Wayne Langel
*Attorney, Agent, or Firm*—Gary P. Topolosky

[57] ABSTRACT

There is provided an improved method for making synthetic hydrotalcite by first reacting powdered magnesium oxide with a high surface area, transition alumina in a solution or suspension to form a meixnerite-like intermediate. This intermediate is then contacted with an anion source such as an acid, and most preferably carbon dioxide, to form the layered double hydroxide which is separated from the suspension by filtering, centrifugation, vacuum dehydration or other known means. On a preferred basis, the transition alumina combined with activated magnesia consists essentially of an rehydratable alumina powder having a surface area of 100 m$^2$/g or greater. To make related double hydroxide compounds, still other reactants such as bromides, chlorides, boric acids, or salts thereof, may be substituted for the carbon dioxide gas fed into this suspension.

28 Claims, No Drawings

TWO POWDER SYNTHESIS OF HYDROTALCITE AND HYDROTALCITE-LIKE COMPOUNDS

CROSS REFERENCE TO RELATED APPLICATIONS

This application is a continuation-in-part of U.S. Ser. No. 08/290,220, filed Aug. 15, 1994, now abandoned, which is a continuation-in-part of U.S. application Ser. No. 08/235, 504, filed Apr. 29, 1994, now U.S. Pat. No. 5,514,361, issued May 7, 1996, the disclosure of which is fully incorporated by reference herein.

BACKGROUND OF THE INVENTION

1. Field of the Invention

This invention relates to the field of making mixed metal hydroxides or layered double hydroxide products. More specifically, the invention relates to an improved two-step method for making hydrotalcite and hydrotalcite-like compounds from dry powder constituents.

2. Technology Review

Hydrotalcite exists in both a natural and synthetic form. Naturally occurring deposits have been found in Snarum, Norway and in the Ural Mountains. Typical occurrences are in the form of serpentines, talc schists, or as an alteration product where hydrotalcite forms the pseudomorph of a spinel. Like most ores, natural hydrotalcite is virtually impossible to find in a pure state. Such deposits often contain one or more other minerals including penninite and muscovite.

Several methods are known for making synthetic hydrotalcite in such product forms as a fine powder, −20 mesh granules or as ⅛-inch diameter extradates. One representative method is described in U.S. Pat. No. 3,539,306. There, an aluminum hydroxide, aluminum-amino acid salt, aluminum alcoholate, water soluble aluminate, aluminum nitrate and/or aluminum sulfate are mixed with a magnesium component selected from magnesium oxide, magnesium hydroxide or water-soluble magnesium salt and a carbonate ion-containing compound in an aqueous medium maintained at a pH of 8 or more. The resulting product may be used as a stomach antacid. In this typical neutralization process, a fairly pure, finely sized hydrotalcite particle is formed. A serious disadvantage of this method, however, is its formation of a sodium salt by-product. This salt neutralization process for making hydrotalcites could also produce a brucite-like structure with undesired anions (e.g. sulfate) or cations ($Na^+$) included therein.

In Misra Reissue U.S. Pat. No. 34,164, the disclosure of which is fully incorporated by reference, yet another means for synthesizing hydrotalcite is taught. The method comprises heating magnesium carbonate and/or magnesium hydroxide to form activated magnesia, then combining the activated magnesia with an aqueous solution of aluminate, carbonate and hydroxyl ions.

Other known methods for synthesizing hydrotalcite include: adding dry ice or ammonium carbonate to a thermal decomposition product from a magnesium nitrate-aluminum nitrate mixture, after which intermediate product is subjected to temperatures below about 325° F. and pressures of 2,000 to 20,000 psi. Yet another process, from "Properties of a Synthetic Magnesium-Aluminum Carbonate Hydroxide and its Relationship to Magnesium-Aluminum Double Hydroxide Manasseite, and Hydrotalcite", *The American Mineralogist*, Vol. 52, pp. 1036–1047 (1967), produces hydrotalcite-like materials by titrating a solution of $MgCl_2$ and $AlCl_3$ with NaOH in a carbon dioxide-free system. This suspension is dialyzed for 30 days at 60° C. to form a hydrated Mg—Al carbonate hydroxide having the properties of both manasseite and hydrotalcite.

It is a principal objective of this invention to provide an improved means for making synthetic hydrotalcite and hydrotalcite-like compounds from two or more relatively inexpensive, dry powder components. It is another objective to provide an improved process for making hydrotalcite and related materials with less sodium ion contamination. It is still another objective to provide a method for synthesizing hydrotalcite without depending on the use of any alumina gels. It is still another objective to make hydrotalcite and hydrotalcite-like compounds through the further processing of an improved meixnerite product, itself made by combining activated magnesia with a high surface area, transition alumina.

Yet another principal objective is to make hydrotalcite and hydrotalcite-like compounds in a more environmentally acceptable manner. According to preferred embodiments, the synthetic hydrotalcites made by the methods described hereinbelow yield no by-products other than water. Any remaining discharge waters should be easily disposable due to their low dissolved solids content.

SUMMARY OF THE INVENTION

In accordance with the foregoing objectives and advantages, there is provided an improved method for making synthetic hydrotalcite. The method comprises reacting powdered magnesium oxide with a high surface area, transition alumina in a carboxylic acid-free aqueous suspension or slurry to form meixnerite or a meixnerite-like intermediate. The latter intermediate is then contacted with an anion source such as an acid or acid precursor, most preferably carbon dioxide, to form the layered double hydroxide compound which is separated from the suspension by filtering, centrifugation, vacuum dehydration or other known means. On a preferred basis, the transition alumina so combined with activated magnesia consists essentially of an activated alumina powder having a surface area of about 100 $m^2/g$ or greater. For related double hydroxide formations, still other reactants, such as bromides, chlorides, boric acids, or their salts, are combined with the meixnerite intermediate to make similarly structured, brucite-like layered double hydroxide family members.

DETAILED DESCRIPTION OF PREFERRED EMBODIMENTS

1. Definitions

As used herein, the following terms shall have the meanings provided hereinbelow:

a. "Transition alumina" means a high surface area alumina in a powdered or fine particulate form. One preferred way of defining such alumina materials uses surface area and Loss on Ignition (LOI) measurements. More specifically, an alumina having a Brunauer-Emmett-Teller [or B.E.T.] measured surface area of about 100 $m^2/g$ or more would be considered as having a high surface area and thus qualify as a transition alumina for purposes of this invention. Aluminas having an LOI weight percentage of about 1.5% or more would also qualify under this definition.

One particular preferred type of transition aluminas is referred to as a "rehydratable alumina". It tends to form strong hydroxyl bonds on contact with water and its rehydration reactions are highly exothermic. The average particle sizes for such aluminas may range from 0.01–200μ, with a range of about 0.1 to 10 or 20 micrometers being more preferred.

Certain activated aluminas are more suitable than others for purposes of this invention. Most are high surface area aluminas formed by the rapid calcination of hydrated alumina at temperatures below that required for complete dehydration or calcination. Typically, such aluminas are amorphous (i.e., have no microcrystalline structure) as determined by X-ray diffraction. These powders exhibit an LOI value of about 4–12% by weight, and a BET surface area of about 200–300 m$^2$/g.

b. "Activated magnesia" or activated magnesium oxide refers to the magnesium-based product activated by "soft burning" MgO at one or more temperatures between about 450° and 900° C. This component has a general surface area of about 10–200 m$^2$/g, preferably about 20–150 m$^2$/g and an L.O.I. ranging from 1.0 to 6.0 wt. %. Such criteria distinguishes this reactant from magnesias which have been dead-burned or completely calcined. Although the latter may still produce meixnerite with longer reaction times or under more strenuous reaction conditions, the percent yields from such conditions are significantly lower than those preferred for the present invention.

There are numerous means for making an activated magnesia product to combine with transition aluminas according to the first method step of this invention. For example, commercially sold magnesium carbonate can be heated to drive off carbon dioxide and thus form a reactive magnesia thereby. Magnesium oxide may also be made by: (a) heating natural or synthetic magnesium hydroxides or basic magnesium carbonate, to temperatures between about 380° and 950° C.; or (b) by heating MgCl$_2$ with lime. Various known methods may be used to generate magnesia powders of various particles sizes and/or surface areas.

c. "Hydrotalcite" compounds shall be understood to apply to the structural family of layered double hydroxides whose family members consist of any compound having the formula: A$_w$B$_x$(OH)$_y$C$_z$.nH$_2$O, wherein A represents a divalent metal cation, B a trivalent metal cation, C a mono- to polyvalent anion, and w, x, y, z and n satisfy the following conditions: $0 < z \leq x \leq 4 \leq w \leq 1/2y$ and $12 \geq n \geq 1/2(w-x)$. Preferred embodiments of this family have been identified by the formula: A$_6$B$_2$(OH)$_{16}$C$_z$.4H$_2$O, wherein A is selected from: Mg$^{2+}$, Ni$^{2+}$, Cu$^{2+}$, Ca$^{2+}$, Fe$^{2+}$ and Zn$^{2+}$; B from: Al$^{3+}$, Fe$^{3+}$ and Cr$^{3+}$; and C from an anion list which includes: OH$^-$, Cl$^-$, Br$^-$, NO$_3^-$, CH$_3$COO$^-$, CO$_3^{2-}$, SO$_4^{2-}$, PO$_4^{3-}$, Fe(CN)$_6^{3-}$, Fe(CN)$_6^{4-}$ and some borates, carboxylates and polyoxometallates, with $1/2 \leq z \leq 2$ (depending on the charge of the anion substituted therein). Some references refer to any compound having the aforementioned formulae as "hydrotalcite". For purposes of this invention, however, this family of structural compounds has been divided into various subgroups depending on the divalent and trivalent cations within its alternating brucite-like layers. For example, pyroaurites have the basic formula: Mg$_6$Fe$_2$(OH)$_6$CO$_3$.4H$_2$O. Such compounds are also known as "sjogrenites". Collectively, these other family members have been referred to as "hydrotalcite-like" compounds.

Yet another preferred definition for the term "hydrotalcite" includes any natural or synthetic compound satisfying the formulae: Mg$_6$Al$_2$(OH)$_{16}$CO$_3$.4H$_2$O or Mg$_4$Al$_2$(OH)$_{12}$CO$_3$.3H$_2$O. This compound has sometimes been written as: 6MgO.Al$_2$O$_3$.CO$_2$.12H$_2$O. In its ionic form, hydrotalcite may appear as: [Mg$_6$Al$_2$(OH)$_{16}$]$^{2+}$.[CO$_3$]$^{2-}$.4H$_2$O. The main structural unit for this compound is brucite, or magnesium hydroxide (Mg(OH)$_2$) having the form of an octagonal sheet with Mg ions positioned between multiple (OH) ions which share adjacent edges. By substituting trivalent aluminum ions for some of the divalent magnesium of this structure, sublayers of magnesium and aluminum are created while still maintaining brucite's basic sheet-like structure. To compensate for the charge imbalance from these aluminum ion substitutions, anions (indicated by letter "C" in the foregoing formulae) and water molecules are intercalated therein to form interlayers of (C$_z$.nH$_2$O) between the brucite-like structural layers, with $1/2 \leq z \leq 2$ depending on the anion so intercalated. The anion having the greatest affinity to combine with water in this structure and form hydrotalcite is carbonate (CO$_3^{2-}$). Sulfate (SO$_4^{2-}$) is another compatible anion.

The spacial distribution of carbonate ions within hydrotalcite partially depends on how the Al$^{3+}$ ions substitute for the Mg$^{2+}$ ions therein. Brucite layer spacing is also a function of the amount or degree of aluminum substitution into hydrotalcite's basic structure. As aluminum substitution increases, interlayer spacing decreases due to an increase in the electrostatic attraction between positive hydroxide layers and hydrotalcite's negative interlayers. Interlayer thicknesses may also vary depending on the size and orientation of the anions substituted for some or all of the carbonate ions in hydrotalcite. From preferred embodiments, a hydrotalcite material having a Mg:Al ratio of about 2 (x=0.33) to 3 (x=0.25) or higher is contemplated.

d. "Basic magnesium carbonate" means a dicalcium salt containing hydroxide and carbonate anions in the same powder product, sometimes represented by the formula Mg(OH)$_2$.MgCO$_3$.

e. "Meixnerite" means a hydrotalcite-like, layered double hydroxide material in which all the intercalated anions are hydroxyls.

One generic means for summarizing the reactions believed to occur by the method described herein is as follows:

Step 1. M$_a$O$_b$+Al$_2$O$_3$.gH$_2$O→MX

Step 2. MX+HA→Layered Double Hydroxide+H$_2$O.

On a more preferred basis, the following two steps are believed to occur for hydrotalcite manufacture:

Step 1:

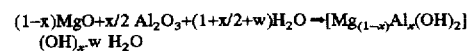

$$(1-x)MgO+x/2\ Al_2O_3+(1+x/2+w)H_2O \rightarrow [Mg_{(1-x)}Al_x(OH)_2](OH)_x.w\ H_2O$$

followed by Step 2:

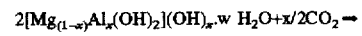
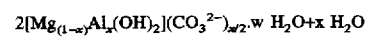

$$2[Mg_{(1-x)}Al_x(OH)_2](OH)_x.w\ H_2O+x/2CO_2 \rightarrow$$
$$2[Mg_{(1-x)}Al_x(OH)_2](CO_3^{2-})_{x/2}.w\ H_2O+x\ H_2O$$

For some dry powder reactants, temperature limitations on the contacting water solution have proven beneficial to overall yield. While Step 1 of the foregoing reaction may proceed at temperatures as low as 25° C. for calcium-containing compounds, they usually proceed best at one or more temperatures between about 80° and 160° C., especially for magesium-containing, layered double hydroxides made by the method of this invention. At such temperatures, yields in excess of about 75% are commonly observed. More preferred reaction temperatures generally run between about 98° and 150° C. Though higher reaction pressures, up to about 8 atmospheres (or atm), have been known to enhance the synthesis of hydrotalcite and hydrotalcite-like compounds according to this invention, more preferred reaction pressures are usually between ambient and 4.7 arms, as determined by the vapor pressure of water.

Suitable end uses for the hydrotalcite products made by this method include acid neutralizers and scavengers, especially for polypropylene and polyethylene manufacturers, adsorbents for heavy metal anions from waste waters, stabilizing components for other polymer systems such as poly (vinyl chloride), flame retarders, smoke suppressers, catalysts, catalyst supports and viscosity control agents.

Further features, objects and advantages of the present invention will be made clearer from the detailed description of examples which follows. It is to be understood, however, that such examples are merely representative of this invention and should not be used to limit its scope in any manner.

EXAMPLES 1-7

Each of the following were conducted using a 1.8 liter capacity, internally stirred reactor charged with 750 ml of deionized water. In each case, after the respective divalent and trivalent metal compounds were added to the water and dispersed therethrough with continuous stirring, carbon dioxide was bubbled into the reactor from a pressurized cylinder. When respective reaction times were completed, the reactor was allowed to cool and excess carbon dioxide gradually vented into the atmosphere. The resulting slurry was then vacuum filtered using a Buchner funnel and a sample of each filtrate was further dried under vacuum before x-ray diffraction analyses were conducted thereon to determine which crystal phases were present in these dried solids.

Comparative Example 1

100 grams of hydromagnesite having the formula $Mg_5(CO_3)_4(OH)_2 \cdot 4H_2O$ and 47 grams of ground aluminum hydroxide having an average particle size of 10.0 μm were charged to the reactor. Carbon dioxide was added until the reactor pressure reached 34.3 atm. The reactor temperature was then maintained between 25°-26° C. for about 4 hours. Analysis of the dried solids removed from this reaction showed the presence of hydromagnesite and alumina as gibbsite but no hydrotalcite.

Comparative Example 2

For this example, another 100 grams of hydromagnesite were charged with 41.7 grams of the same ground $Al(OH)_3$ as in Example 1. Liquid carbon dioxide was added until the reactor pressure reached 36.4 atm. The reactor temperature was then maintained between 48°-53° C. for about 4 hours. Analysis of the dried solids removed from this reaction again showed the presence of hydromagnesite and gibbsite but no hydrotalcite.

Comparative Example 3

The same quantity of hydromagnesite and ground $Al(OH)_3$ used for Example 2 were again charged to a reactor for this Example. With 43.9 atm of carbon dioxide added, the reactor charged for 4 hours at 90° C. still showed no sign of hydrotalcite in the recovered solids.

EXAMPLE 4

For this Example, 100 grams of the same hydromagnesite as before were charged with 31.0 grams of a rehydratable alumina having an average particle size of 2.0 μm. The slurry was stirred at room temperature for 3 hours while enough liquid carbon dioxide was added to raise the overall reactor pressure to 40.1 atm. The whole system was then heated to 50° C. for 2 hours. The dried filter cake from this reaction was found to contain major amounts of hydrotalcite by x-ray diffraction analysis.

EXAMPLE 5

For this Example, 100 grams of the same hydromagnesite as before were charged with 38.7 grams of a pseudoboehmite sold by Vista Chemical Co. under the tradename Catapal® SB, said material consisting of 65 μm diameter agglomerates of 0.1 μm basic particles. Enough carbon dioxide was added to take overall reactor pressure to 42.5 atm. The system was then kept between 48°-52° C. for 4 hours. X-ray diffraction analysis of the resulting filter cake showed that major amounts of hydrotalcite was present.

EXAMPLE 6

The same quantities of hydromagnesite and pseudoboehmite used for Example 5 were again charged to a reactor for this Example. With 52.0 atm of carbon dioxide added, the reactor charged for 4 hours at 90° C. resulted in a filter cake which had major amounts of hydrotalcite present (by x-ray diffraction analysis).

EXAMPLE 7

The same quantities of hydromagnesite and rehydratable alumina used for Example 4 were again charged to a reactor, but for this Example no additional carbon dioxide was added thereto. The system was heated to 50° C. for 2 hours. The resulting filter cake was analyzed to contain major amounts of hydrotalcite as well. However, the degree of hydromagnesite conversion for Example 7 was less than in Example 4 based on a comparison of x-ray diffraction peak intensities for these products.

EXAMPLES 8-13

For each of these examples, about 70 grams of MgO and 45.6 grams of rehydratable $Al_2O_3$ were mixed with 1200 ml of deionized water in a round-bottom flask to form a slurry. The slurry was then stirred and heated to atmospheric boiling. The area in the flask over the slurry was purged with nitrogen to prevent reaction with $CO_2$ from the air. After six (6) hours in the reactor, samples were removed and analyzed. Considerable meixnerite was found in these samples. After 22 hours at boiling, conversion was nearly complete. Several portions of this slurry were then cooled below 40° C. and treated with carbon dioxide gas or atmospheric air for converting the meixnerite to hydrotalcite. Samples removed from this slurry were analyzed and shown to contain major amounts of hydrotalcite. For Example 11, an oxalate was formed by adding oxalic acid to the meixnerite slurry at about 26°-30° C. A borate form of hydrotalcite was made by adding boric acid to the meixnerite slurry for Example 12 and a stearate form was made by contacting meixnerite with stearic acid per Example 13.

Having described the presently preferred embodiments, it is to be understood that the invention may be otherwise embodied within the scope of the appended claims.

What is claimed is:

1. A method for making a layered double hydroxide powder comprising:

(a) reacting at least one trivalent metal oxide powder and at least one divalent metal compound selected from the group consisting of a hydroxide, oxide, carbonate and mixtures thereof, in a carboxylic acid and carboxylate ion-free, aqueous suspension to form a double hydroxide intermediate;

(b) contacting the double hydroxide intermediate with an anion source to form a layered double hydroxide; and (c) separating the layered double hydroxide from the suspension.

2. The method of claim 1 wherein the divalent metal compound is selected from the group consisting of: a magnesium oxide, hydroxide, carbonate and mixtures thereof, a zinc oxide-containing compound, a copper oxide-containing compound, a nickel oxide-containing compound, an iron oxide-containing compound, a calcium oxide-containing compound, a manganese oxide-containing compound and mixtures thereof.

3. The method of claim 1 wherein the divalent metal compound is selected from the group consisting of a magnesium oxide, a magnesium hydroxide, a magnesium carbonate and mixtures thereof.

4. The method of claim 3 wherein the powdered divalent metal compound is selected from the group consisting of: basic magnesium carbonate, magnesium oxide, hydromagnesite and mixtures thereof.

5. The method of claim 1 wherein the powdered divalent metal compound consists essentially of hydromagnesite.

6. The method of claim 1 wherein the trivalent metal oxide powder is a powder selected from the group consisting of: an aluminum oxide-containing compound, an iron oxide-containing compound, a chromium oxide-containing compound and mixtures thereof, said powder having a B.E.T. surface area of about 100 $m^2/g$ or more.

7. The method of claim 6 wherein the trivalent metal oxide powder consists essentially of a transition alumina.

8. The method of claim 7 wherein the transition alumina consists essentially of a rehydratable alumina powder.

9. The method of claim 7 wherein the transition alumina consists essentially of an activated alumina having a BET surface area of about 200 $m^2/g$ or greater.

10. The method of claim 1 wherein the anion source in step (b) is selected from the group consisting of: carbon dioxide; a carbonate-containing compound and mixtures thereof.

11. The method of claim 10 wherein the anion source consists essentially of an acid.

12. The method of claim 10 wherein the anion source consists essentially of an ammonium salt.

13. The method of claim 10 wherein the anion source consists essentially of carbon dioxide.

14. The method of claim 1 wherein the double hydroxide intermediate contacting step (b) consists essentially of bubbling carbon dioxide gas through the suspension at an elevated pressure.

15. A method for making hydrotalcite at one or more temperatures at or below about 160° C., said method comprising:

(a) reacting a magnesium-containing powder and a transition alumina powder in a carboxylic acid and carboxylate ion-free, aqueous suspension to form a meixnerite intermediate;

(b) contacting the meixnerite intermediate with a carbonate-containing ion to form a hydrotalcite compound; and (c) separating the hydrotalcite compound from the suspension.

16. The method of claim 15 wherein the magnesium-containing powder is selected from the group consisting of: basic magnesium carbonate, magnesium oxide, hydromagnesite and mixtures thereof.

17. The method of claim 16 wherein the magnesium-containing powder consists essentially of hydromagnesite.

18. The method of claim 16 wherein the magnesium-containing powder consists essentially of an activated magnesium oxide powder.

19. The method of claim 15 wherein the transition alumina consists essentially of a rehydratable alumina powder.

20. The method of claim 15 wherein the transition alumina consists essentially of an activated alumina having a BET surface area of about 100 $m^2/g$ or greater.

21. The method of claim 15 wherein the carbonate-containing ion in step (b) is selected from the group consisting of: $CO_2$, $HCO_3^-$ $CO_3^{2-}$ and mixtures thereof.

22. The method of claim 21 wherein the carbonate-containing ion consists essentially of carbon dioxide.

23. A method for making a layered double hydroxide powder comprising:

(a) reacting meixnerite in a carboxylic acid and carboxylate ion-free, aqueous suspension with an anion source to form a layered double hydroxide; and (b) separating the layered double hydroxide from the suspension.

24. The method of claim 23 wherein the anion source in step (a) is selected from the group consisting of: carbon dioxide; a carbonate-containing compound; and mixtures thereof.

25. The method of claim 23 wherein the anion source consists essentially of carbon dioxide.

26. A method for making hydrotalcite at one or more temperatures at or below about 160° C., said method comprising:

(a) reacting meixnerite in a carboxylic acid and carboxylate ion-free, aqueous suspension with a carbonate-containing ion to form a hydrotalcite compound; and (b) separating the hydrotalcite compound from the suspension.

27. The method of claim 26 wherein the carbonate-containing ion in step (a) is selected from the group consisting of: $CO_2$, $HCO_3^-$ $CO_3^{2-}$ and mixtures thereof.

28. The method of claim 26 wherein the carbonate-containing ion consists essentially of carbon dioxide.

* * * * *